US005741665A

United States Patent [19]
Kato et al.

[11] Patent Number: 5,741,665
[45] Date of Patent: Apr. 21, 1998

[54] LIGHT-REGULATED PROMOTERS FOR PRODUCTION OF HETEROLOGOUS PROTEINS IN FILAMENTOUS FUNGI

[75] Inventors: Elie K. Kato, Honolulu; W. Dorsey Stuart, Kaneohe, both of Hi.

[73] Assignee: University of Hawaii, Honolulu, Hi.

[21] Appl. No.: 240,372

[22] Filed: May 10, 1994

[51] Int. Cl.[6] .............................. C12N 1/15; C12N 15/09; C12N 15/11; C07H 21/04
[52] U.S. Cl. ...................... 435/69.1; 435/254.4; 536/24.1
[58] Field of Search ............................... 435/69.1, 254.4; 536/24.1

[56] References Cited

U.S. PATENT DOCUMENTS 5,187,079   2/1993   Free et al. ............................... 435/69.1

FOREIGN PATENT DOCUMENTS 9325663   12/1993   WIPO .

OTHER PUBLICATIONS

Schmidhauser et al. (1994 Apr. 22) "Characterization of al-2, The Phytoene Synthase Gene of *Neurospora crassa*" J Biol Chem 269: 12060–12066.

Letouvet-Pawlak et al (1990) "Comparsion of β-galactosidase Production by Two Inducible Promoters in *Myxococcus xanthus*" Res. Microbiol 141: 425–435.

Collins et al (1991) "An Inducible Gene Expression System for *Neurospora crassa*." Emzyme Microb. Technol. 13: 400–403.

Moir et al. (1982) "Molecular Characterzation of Double-Stranded cDNA Coding for Bovine Chymosine" Gene 19:127–138.

Stadler et al (1991) "Spontaneous Mutation at The mtr Locus of Neurospora: The Spectrum of Mutant Types" Genetics 129: 39–45.

Harding et al., "Photoregulation of the Carotenoid Biosynthetic Pathway in Albino and White Collar Mutants of *Neurospora crassa*", *Plant Physiol.*, 68:749–49 (1981).

Nelson et al., "Molecular Cloning of a *Neurospora crassa* Carotenoid Biosynthetic Gene (Albino–3) Regulated by Blue Light and the Products of the White Collar Genes", *Mol. Cell. Biol.*, 9:1271–76 (1989).

Schmidhauser et al., "Cloning, Sequence, and Photoregulation of al–1, a Carotenoid Biosynthetic Gene of *Neurospora crassa*", *Mol. Cell. Biol.*, 10:5064–70 (1990).

Baima, "Photoinduction of albino–3 Gene Expression in *Neurospora crassa* Conidia", *J. Photochem. Photobiol.*, 15:233–38 (1992).

*Primary Examiner*—Jasemine C. Chambers
*Assistant Examiner*—Scott D. Priebe
*Attorney, Agent, or Firm*—Morrison&FoersterLLP

[57] ABSTRACT

The al-3 and related promoters can be used to provide light-regulated recombinant production of heterologous proteins in filamentous fungi. Expression systems utilizing these promoters can be placed in vectors which also optionally contain selectable marker means.

9 Claims, 7 Drawing Sheets al-3 promoter -> List

DNA sequence   1237 b.p.   AAGCTTGCATGC ... GAGCTCGAATTC   linear

```
           10         20         30         40         50         60
            |          |          |          |          |          |
   1 AAGCTTGCAT GCCTGCAGct ttatgcactc ggcgcttccc tgtgtcaagt cttgcatcgc    60
  61 cgacagacgt gcacaaagtc gccgcgtgtg tgcttgaatc cgttgccatc gagtgctata   120
 121 taaagtgtcc agacgtcccc ttcctaaat cgtcttgaat gtcccaatat gcatggatga   180
 181 agtggactga actcgcacgt tctgaccgct ttctgaata ccctaattt gcgcaaggtc   240
 241 ccacaacagc cgacctcgtt caacatctct taccacctac agttacctac ccatttga   300
 301 cgagccctt accagcaaca acgcgtcaat ccttggttat tctctgtttg ttcatgtcgg   360
 361 tctgaagccc tgacaagaca acatcacagc agaaattga acgcttttcc acaaactaca   420
 421 aggtgagaaa cctccccag tttcatccc tagaagatgc cggtttcagc agggagctcc   480
 481 cgacaaagag cgcgcgagac gggatcgccc gttcgatctt cagttgtgaa gctctttgt   540
 541 cccctgtga gagctcccgc cccgcatctg aaacccace acgctacttt caggtgtcgt   600
 601 cggggtttca ttcttgcaaa catgtcctcc gtcggccgcc caagaagtct ccgcacttgc   660
 661 aatcacctg catccactgc cagggaaag gaaaggacag gcaggtcaga tctgaggaaa   720
 721 gcgctacggc agcttgatcc gatttgtccg cccctagttt cccttctgat cgcttccgag   780
 781 atccagtgac gatggctggc atgtgacaag atcgggggat gcaatctcga gtttttctga   840
 841 acctagcaga agagaggctt cttccattc ggcgtattct ttgctgaccc cagatacaga   900
 901 tagatctctt ggcctttgtt cactcagcag gcaagcaggg caaatccccc ttctcatagc   960
 961 aaagtgaggt cgattgctgt cgattggcac acgacctgtc aagcggtatt atcgtcatag  1020
1021 cgtgcgggta tcgaatattg ccccgagac cgtgaagctt gcctccggtt gtcacacagc  1080
1081 acgtcaagta attataagaa gccagccaga gcgccggcca cttggatca gacgacgcac  1140
1141 ggggttagca tcctctacag taccgacggg tttccaataa GTCGACTCTA GACTTAATTA  1200
1201 AGGATCCGGC GCGCCCCCGG GTACCGAGCT CGAATTC                           1237
            |          |          |          |          |          |
           10         20         30         40         50         60
```

FIG. 1 pLRN (LIGHT REGULATED NEUTRAL SYSTEM) ~6,576 bp
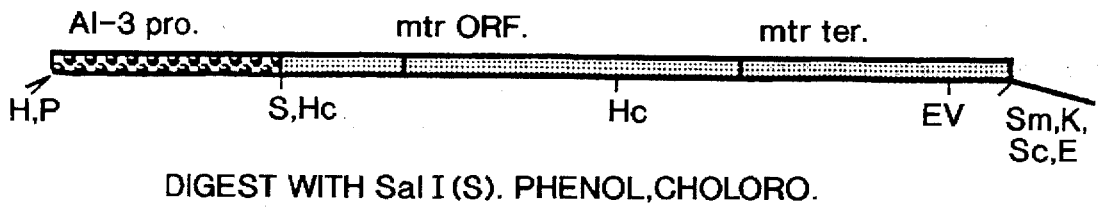
DIGEST WITH Sal I (S). PHENOL,CHOLORO.
CHYMOSIN GENE ISOLATED FROM pBC1 8HXH. RELEASED WITH
Xho I AND Sal I DOUBLE DIGEST.
FRAGMENTS WERE LIGATED TOGETHER Sal I TO Xho I, Sal I TO Sal I
FOR PROPER ORIENTATION. MAKING pCLRN (Chy,LIGHT,REG,NEUT).
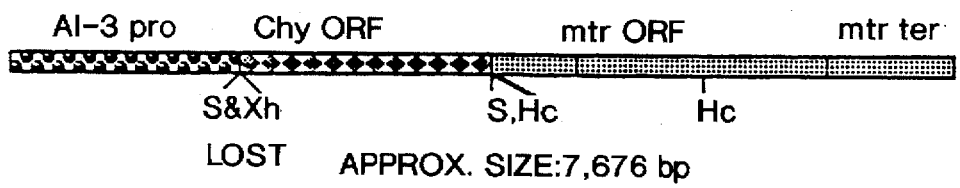
DIGEST WITH HincII TO DISRUPT mtr PROTEIN. RELIGATE TO ITSELF
TO MAKE pLRC.
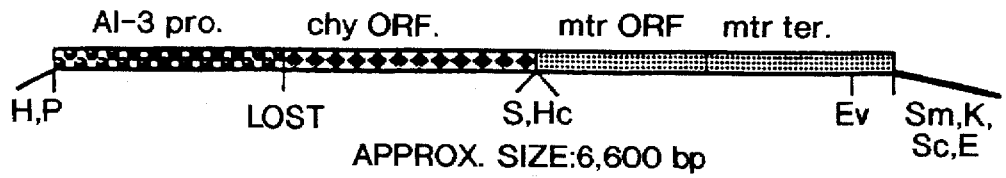
FIG. 6 pBC18XH -> List

DNA sequence    1240 b.p.    gaattcgagctc ... gcagccaagctt    linear

```
             10         20         30         40         50         60
              |          |          |          |          |          |
   1 gaattcgagc tcggtacccg ggatcctct agcctcgagg ctagagtctc ccggctgac      60
  61 ccagatccaa gatgaggtgt ctcgtgtgc tacttgctgt cttcgctctc tcccagggcg    120
 121 ctgagatcac caggatccct ctgtacaaag gcaagtctct gaggaaggcg ctgaaggagc   180
 181 atgggcttct ggaggacttc ctgcagaaac agcagtatgg catcagcagc aagtactccg   240
 241 gcttcgggga ggtggccagc gtgcccctga ccaactacct ggatagtcag tactttggga   300
 301 agatctacct cggaccccg tcaccgtgct gtttgacact ggctcctctg                360
 361 actttctggt accctctatc tactgcaaga gcaatgcctg caaaaaccac cagcgcttcg    420
 421 acccagaaaa gtcgtccacc ttccagaacc tggcaagcc cctgtctatc cactacggga    480
 481 caggcagcat gcagggcatc ctaggctatg acaccgtcac tgtcttccaac attgtggaca   540
 541 tccaggagac agtaggcctg agcacccagg agcccgggga cgtccgctc tatgccgaat    600
 601 tcgacgggat cctggggatg gcctaccct cgctcgcctc agagtactcg ataccgtgt      660
 661 ttgacaacat gatgaacagg cacctggtgg cccaagacct gttctcggtt tacatggaca   720
 721 ggaatggcca ggagagcatg ctcacgctgg gggctctga gttcactgga tacacaggt     780
 781 ccctgcactg gtgtgccgtg acagtgcagc agtactggca gttcactgtg gacagtgtca    840
 841 ccatcagcgg tgtggttgtg gcctgtgagg gtgctgtca ggccatcctg gacacgggca    900
 901 ccctccaagc tggtcgggcc agcagcgaca tcctcaacat ccagccagcc attggagcca   960
 961 cacagaacca gtacgatgag tttgacatcg actgcgacaa cctgagctac atgcccactg   1020
1021 tggtctttga gatcaatgtt aaaatgtacc cactgacccc ctccgcctat accagccaag   1080
1081 accagggctt ctgtaccagt ggcttccaga gtgaaaatca ttcccagaaa tggatcctgg   1140
1141 gggatgtttt catccagcag tattacagcg tctttgacag ggccaacaac ctcgtggggc   1200
1201 tggccaaagc catctgactc gtcgacctgc agccaagctt                          1240
              |          |          |          |          |          |
             10         20         30         40         50         60
```

FIG. 7

LIGHT-REGULATED PROMOTERS FOR PRODUCTION OF HETEROLOGOUS PROTEINS IN FILAMENTOUS FUNGI

TECHNICAL FIELD

The invention relates to recombinant production of heterologous, especially eucaryotic, proteins in filamentous fungal hosts. In particular, it relates to expression constructs which utilize light-regulated fungal promoters.

BACKGROUND ART

It has been known for many years that exposure to light activates the transcription of a number of genes in the common bread mold, Neurospora. Several of these genes produce products which are essential enzymes in the synthetic pathway of carotenoids. A number of distinct genetic mutants in this pathway (designated Albino-1, -2 and -3 or al-1, al-2 and al-3) were described in a paper by Harding, R. W. et al. *Plant Physiol* (1981) 68:745–749. The genes associated with these mutations are light-regulated, and the genes associated with all three of the al-1, al-2 and al-3 mutants have been cloned (Nelson, M. A. et al. *Mol Cell Biol* (1989) 9:1271–1276; Schmidhauser, T. J. et al. *Mol Cell Biol* (1990) 10:5064–5070).

The al-3 gene controls the production of geranyl geranyl pyrophosphate synthetase. Geranyl geranyl pyrophosphate is precursor for carotenoids and xanthophylls. Previous work has shown that the synthesis of this intermediate is controlled at a transcriptional level and that a 30-minute pulse of light causes a 15–45 fold coordinated increase in the transcription of the three genes in the carotenoid biosynthetic pathway. The conditions for activating the al-3 promoter using light are known, for example, as described by Baima, S. et al. *J Photochem. Photobiol.* (1992) 15:233–238.

Because it is often convenient to regulate the expression of genes encoding heterologous proteins in recombinant production systems, placing the relevant coding sequence under control of a light-regulated promoter would offer a simple and effective way to control expression and adapt its timing to the physiological status of the host. Heretofore, there has been no utilization of this means of regulation in expression systems associated with filamentous fungal hosts. The present invention provides such a regulated system.

DISCLOSURE OF THE INVENTION

The invention provides expression systems for heterologous proteins in filamentous fungi which can be regulated by the presence or absence of light. These expression systems place the nucleotide sequence encoding a heterologous protein under control of the promoter associated with the al-1, al-2 or al-3 gene. Advantageously, the expression system is contained on a nucleic acid molecule that further comprises a nucleotide sequence which, in the context of the fungal host used, will provide a selectable marker function.

Accordingly, in one aspect, the invention is directed to a nucleic acid molecule which comprises a first nucleotide sequence encoding a heterologous protein operably linked to the al-1, al-2 or al-3 promoter and optionally further comprises a second nucleotide sequence that provides for selectable marker means in the fungus chosen.

In other aspects, the invention is directed to filamentous fungi modified to contain the nucleic acid molecules of the invention and to methods to produce heterologous proteins by culturing these fungi.

BRIEF DESCRIPTION OF THE DRAWINGS

FIG. 1 (SEQ ID NO: 1) shows the nucleotide sequence of the al-3 promoter insert used to construct the plasmids of the invention.

FIG. 6 is a diagram showing the construction of pLRC.

FIG. 7 (SEQ ID NO: 2) shows the nucleotide sequence of the chymosin open reading frame.

MODES OF CARRYING OUT THE INVENTION

Figure 2:
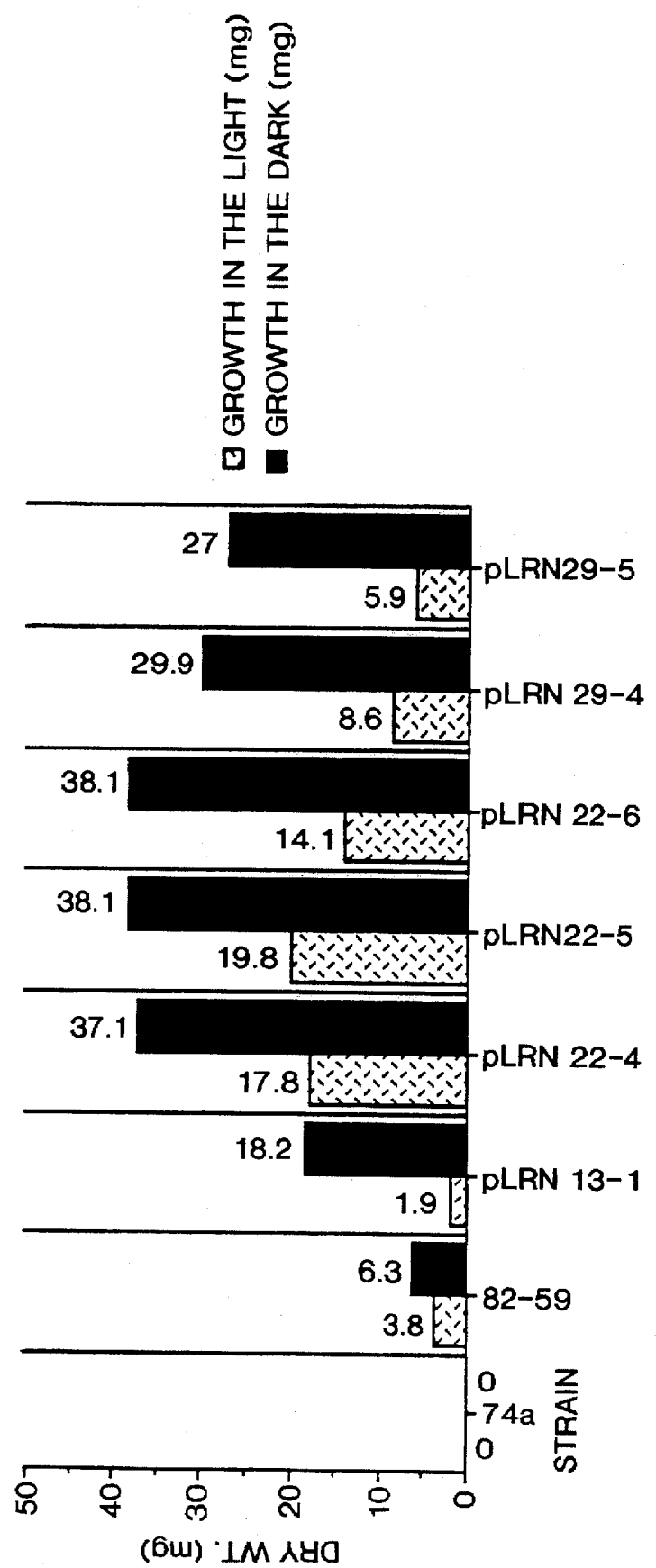
FIG. 2 shows the effect of light on growth of *N. crassa* cultures transformed with various plasmids containing the open reading frame (ORF) of the mtr gene under control of the al-3 promoter.

The invention provides expression systems useful when filamentous fungi are used as recombinant hosts. "Filamentous fungi" refers to fungi that can form a mycelium through a mass of branching, interlocking filaments. Although these branches may be interrupted by cross-walls, the passage of cytoplasm between compartments is possible. Both sexual and asexual reproduction occur in these fungi. In asexual reproduction, spores known as "conidia" are borne externally at the tips of budding projections formed at various locations along the filaments. The families represented by filamentous fungi include Phycomycetes, Ascomycetes, Basidiomycetes and Deuteromycetes. The most popular family is the Ascomycetes which includes the genera Neurospora, Aspergillus and Penicillium. Particularly preferred hosts include *A. nidulans*, *A. niger* and *N. crassa*, especially *N. crassa*.

THE LIGHT-REGULATED EXPRESSION SYSTEM

The nucleic acid molecules of the invention comprise an expression system utilizing the al-1, al-2 or al-3 promoter operably linked to a nucleotide sequence encoding a heterologous protein. The expression system is typically supplied along with a selectable marker means. The selectable marker means may reside on an additional vector or may be included in the nucleic acid molecule which contains the expression system. The nature of the selectable marker means will depend on the nature of the host and the culture conditions.

The expression system itself will comprise the required promoter as well as, if desired, other features which help regulate expression such as enhancers, terminator sequences, polyadenylation sequences and the like as is understood in the art. Means for constructing such expression systems from nucleic acid of known sequence is well understood and employs conventional techniques such as those set forth in Maniatis et al., *Molecular Cloning: A Laboratory Manual* (1982); Gover, D. N. et al. *DNA Cloning: A Practical Approach* (1985) Vols. I and II and other standard texts commonly available to practitioners.

In general, the al-1, al-2 or al-3 promoter is placed in operable linkage with a desired coding sequence for expression. Suitable coding sequences are those for a variety of proteins including enzymes such as urokinase, tissue plasminogen activator, or collagenase; hormones such as human, bovine or chicken growth hormones, gonadotropins such as follicle stimulating hormone, luteinizing hormone, thyroid stimulating hormone or human chorionic gonadotropin, insulin, including human, porcine or bovine insulin, ACTH, prolactin and the like; peptides that mediate physiological functions such as atrial natriuretic peptide, erythropoietin, bradykinin and brain natriuretic peptide; cytokines such as the interleukins, colony stimulating factors; immunoglobulins and fragments thereof; certain toxins, such as ricin or diphtheria toxin; enzymes of industrial importance such as proteases, oxidases, peroxidases and the like; receptor proteins such as thrombin receptor, calcium receptors and the like; nutritional and structural proteins such as sulfur-rich proteins or collagen; growth factors such as TGFα and TGFβ, PDGF, EGF, IGF and FGF; and, in general, any protein whose recombinant production is desired and for which a coding nucleotide sequence can be obtained.

Some of the desired proteins may be heterodimers; in this instance, multiple expression systems involving the promoters of the invention will be used. Both subunits of the heterodimer may be produced by a single vector, or multiple vectors may be used for transformation.

The constructs may be designed, as is generally recognized, to provide a signal sequence for secretion of the desired protein into the culture medium, or the protein may be produced intracellularly. If desired, the protein may be designed as a part of a fusion protein, which can later be cleaved to yield the desired product. Methods for operably linking the promoters of the invention to the desired coding sequence in the above-mentioned environments are generally understood in the art.

SELECTABLE MARKERS

As the filamentous fungal hosts need to be modified to accommodate expression systems of the invention, it is desirable to include a selectable marker in the transformation protocol. The selectable marker can be placed on the same vector as that which contains the expression system of the invention, or may be part of an additional vector used to cotransform the host. The appropriate choice of selectable marker will depend on the nature of the host. A straightforward choice might be, for example, an expression system which produces an enzyme responsible for an antibiotic resistance against an antibiotic to which the host is susceptible, such as benomyl. Alternatively, if a host is chosen with, for example, a nutritional deficiency, the wild-type gene can be used to replace the deficiency. To do so, however, requires a suitable mutant.

Although mutants can be prepared generally, the better studied species of filamentous fungi are preferred because numerous mutants are readily available which make design of transformation vectors containing means for selection more diverse. For example, one very simple method for selection utilizes a mutant host with a requirement for a particular nutrient where the selectable marker means is provided by replacing the defective gene which accounts for this nutritional requirement. As an illustration, if a mutant unable to grow in the absence of histidine is used as a host, successful transformants can be selected using as a "marker" nucleic acid containing the wild type of the gene that is defective in the mutant and growing the transformed cells on minimal media. Only the successful transformants will be able to grow in the absence of histidine. Similar mutations which result in dependence on the presence of other amino acids or other nutrients in the media are also known. In *N.*

*crassa,* for instance, known mutants include mutants which have specific nutritional requirements. Examples of useful nutrient requirements and the relevant mutants include:

(1) amino acids such as histidine (his-1 through -7 mutants), proline (aga mutants), arginine (arg-1 mutants), citrulline (arg-11 mutants), asparagine (asn mutants), choline (chol-1 and chol-2 mutants), cysteine (cys-1 mutants), glutamine (gln-1 mutants), leucine (leu-1 through -4), lysine (lys-2, -4 and -5), methionine (mac mutants and met-6, -9 and -10 mutants), and threonine (thr-2 and -3 mutants);

(2) mixtures of aromatic amino acids, such as a mixture of p-aminobenzoic acid, tyrosine, tryptophan, and phenylalanine (required by all aro strains except aro-6, aro-7 and aro-8), a mixture of tryptophan and phenylalanine (required for aro-6 mutants), a mixture of isoleucine and valine (required for ilv-1, -2 and -3), and a mixture of phenylalanine and tyrosine (required for pt mutants);

(3) vitamins such as pantothenic acid (pan-1 mutants) and thiamine (thi-2 and thi-4 mutants);

(4) purine bases such as adenine (ad-2 through ad-4 and ad-8 mutants), hypoxanthine (ad-2 and ad-3 mutants), inosine, and guanine or guanosine (gua-1 or -2 mutants);

(5) pyrimidine bases such as uracil (pyr-1 through pyr- 6);

(6) saturated fatty acids (cel mutants) or unsaturated fatty acids such as $C_{16}$ or $C_{18}$ fatty acids having a double bond in the cis conformation at either the 9- or 11-position, fatty acids with a double bond in the trans configuration at the 9-position, and fatty acids with multiple cis double bonds interrupted by methylene bridges (ufa-1 and -2);

(7) physiologically important ions such as potassium (trk);

(8) sugar alcohols such as inositol (acu mutants and inl mutants) and glycerol; and (9) other organic entities such as acetate (ace mutants), α-ketoglutarate, succinate, malate, formate or formaldehyde (for mutants), p-aminobenzoic acid (pab-1, -2 and -3 mutants), and sulfonamide (sfo mutants at 35° C.).

One specific example based on a nutritional requirement is the Arg B+ gene coding for the enzyme ornithine transcarbamylase. This enzyme is present in wild type *A. niger.* Mutants lacking this enzyme (Arg B-strains) can be prepared by usual non-specific techniques, such as treatment with ultraviolet radiation, followed by screening based on an inability to grow on minimal medium, coupled with an ability to grow on a medium containing arginine. Fungi containing this genome will grow on minimal medium if they also include an ArgB+ nucleus.

Other selectable markers confer resistance to toxins or to other adverse culture conditions such as high temperature. Specific examples of noxious chemicals that can exert a toxic effect include acriflavine (resistance conferred by acr generally, with the presence of the shg gene being required for resistance by acr-4 and acr-6); 3-amino-1,2,4-triazole (resistance conferred by acr-2, atr-1, cpc, leu-1 or leu-2)); dyes such as malachite green (resistance conferred by acr-3); caffeine (resistance conferred by caf-1); purine analogs (resistance to 8-azaadenine and 2,6-diaminopurine conferred by aza-1; resistance to 8-azaadenine and 8-azaguanine conferred by aza-2; resistance to 8-azaguanine and 6-mercaptopurine conferred by aza-3; resistance to 6-methylpurine conferred by mep(3) and mep(10); cyanide (insensitivity conferred by cni-1 in the first 24 hours of growth); tetrazolium (resistance conferred by cya-6 and cya-7); cycloheximide (resistance conferred by cyh-1, -2 and -3); chromate (resistance conferred by cys-13); 2-deoxy-D-glucose (resistance conferred by dgr); edeine (resistance conferred by edr-1 and -2); ethionine (resistance conferred by eth-1, by nap in the presence of p-fluorophenylalanine, and by oxD if the ethionine is in the D form); fluoro compounds such as 5-fluorodeoxyuridine, 5-fluorouracil, and 5-fluorouridine (resistance to all three conferred by fdu-2; resistance to 5-fluorouracil being conferred by uc-5 in an ammonia-free minimal medium; resistance to 5-fluorodeoxyuridine and 5-fluorouridine being conferred by ud-1), and fluorophenylalanine (resistance conferred by fpr-1 through -6 under certain conditions); 8-azaadenine (resistance conferred by mts); methyl methane sulfonate (insensitive or marginally sensitive for upr-1); surface-active agents such as dequalinium chloride, cetyltrimethyl ammonium bromide, and benzalkonium chloride (resistance conferred by sur-1); and metal ions such as vanadate (resistance conferred by van).

Also useful are genes conferring resistance to extremes in various environmental conditions such as a high or low temperature, the lack of oxygen (resistance conferred by an), constant light (resistance conferred by lis-1, -2 and -3) or the absence of light, UV radiation, ionizing radiation, and high or low osmotic pressures.

Many strains may be obtained from the Fungal Genetics Stock Center (FGSC). Other useful strains can be prepared using known techniques. For example, a strain having the characteristics of *A. niger* (ATCC 46951) can be prepared by mutagenizing with UV light to form an isolate that requires ornithine or arginine for growth in a defined minimal media. This strain, which lacks ornithine carbamoyl transferase, has been called arg B (350(-)52). Media for growing *A. niger* or *A. nidulans* are described by Cove, *Biochim Biophys Acta* (1966) 113:51–56.

However, other selectable marker systems can also be used, such as the inclusion of genes which confer resistance to toxic substances or other detrimental culturing conditions. For example, genes encoding proteins which confer resistance to antibiotics can be used where selection is conducted on media containing the antibiotic. In the case of filamentous fungi, such antibiotics include benomyl.

More complex systems of selection involve inactivation of endogenous genes that confer susceptibility to poisons. For example, illustrated herein is selection by inactivation of the endogenous mtr locus which confers susceptibility to p-fluorophenyl-alanine (pfpa) or 4-methyltryptophan (4-MT). Inactivation occurs by homologous recombination into the mtr locus so as to disrupt its function. Homolgous recombination in filamentous fungi is well established. See, e.g. Asch, D. K. et al. *Mol Gen Genet* (1990)221:37–43; Asch, D. K. et al. *Genetics* (1992) 130:737–748. An alternative approach would utilize inactivation of the endogenous pmb locus which confers sensitivity to canavanine. For these methods of selection, only hosts homokaryotic for transformation are selected. Since filamentous fungi can harbor a multiplicity of nuclei in what is essentially a single cytoplasm, if any one of the nuclei contains an intact gene conferring sensitivity, the fungus will fail to survive in the presence of the toxin.

Thus, in one particularly preferred embodiment, the expression system of the invention may be inserted into a vector which accomplishes homologous recombination into the mtr locus. In this case, preferably, regions of the mtr gene which are insufficient to provide the product of the mtr gene, but sufficient to promote homologous recombination are contiguous with the expression system of the invention or with the nucleotide sequence encoding the desired heterologous protein. Vectors which provide such mtr sequences and means for employing these vectors to effect homologous recombination and thus resistance to pfpa are described in copending application Ser. No. 08/105,448 filed Aug. 12, 1993 the contents of which are now published in PCT application WO 93/25663 and incorporated herein by reference. Described in this application is a vector, there designated pXpress, which provides insertion sites for either the coding sequence for the desired protein or the expression system for the protein or both into the mtr gene such that homologous recombination of the vector with the endogenous mtr confers resistance to this toxin.

Systems of selection which are more subtle in their design may also be used. For example, a double mutant which contains a nonfunctional mtr gene (mtr⁻) and which also is unable to synthesize tryptophan can be selected for transformation by using the functional mtr gene as a marker and culturing the transformants in a medium containing high levels of arginine along with tryptophan. Since the mutant requires tryptophan for growth, it must transport tryptophan from the medium. There are two possible gene products which permit transport of tryptophan: the mtr gene product and the pmg gene product. However, arginine competes for pmg, so the tryptophan can be transported effectively only if a functional mtr gene is present. Thus, only successful transformants will grow on minimal medium containing a tryptophan supplement along with high levels of arginine.

Thus, employing this strategy, the mtr gene sequences can also provide for selection by encoding a product which restores a nutritional deficiency under specified conditions. The vectors described in the above-referenced copending application Ser. No. 08/105,448 and PCT publication WO 93/25663 can also be manipulated to provide the mtr product for such selection procedures.

TRANSFORMATION AND CULTURE

Standard techniques for transformation of filamentous fungi and culturing the fungi are well known in the art. An extensive review of techniques as applied to *N. crassa* is found, for example in Davis and de Serres, *Methods Enzymol* (1971) 17A:79–143. Standard procedures are generally used for the maintenance of strains and the preparation of conidia. Mycelia are typically grown in liquid cultures for about 14 hours (25° C.), as described in Lambowitz et al., *J Cell Biol* (1979) 82:17–31. Host strains can generally be grown in either Vogel's or Fries minimal medium supplemented with the appropriate nutrient(s), such as, for example, histidine; arginine; phe, tyr, and/or trp (each about 80 µg per ml); p-aminobenzoic acid (about 2 µg per ml); and inositol (about 0.2 mg per ml).

Since the promoters of the invention are regulated by light, the cultures can be grown under conditions of darkness until expression is desired. The expression systems can be activated by illuminating the cultures using light radiation which contains blue wavelengths suitable for such activation, as described by Harding, R. W. and Turner, R. V., *Plant Physiol* (1981) 68:745–749 cited above.

When expression has been activated and the desired protein produced, the protein may be recovered from the culture using techniques generally recognized in the art. If the protein is produced intracellularly, the cells are lysed and the lysate subjected to suitable separation and purification procedures. If the protein is secreted into the medium, the medium can be removed and the secreted protein purified using conventional techniques such as size exclusion, ion exchange chromatography, reverse phase chromatography, differential centrifugation, and the like. Suitable protocols will depend on the nature of the protein product.

If the protein is provided as a fusion protein, it is preferable that a protease site be inserted into the sequence so that liberation of the mature protein is a simple matter of treatment with the appropriate protease.

EXAMPLES

The following examples are intended to illustrate but not to limit the invention.

Example 1
Construction of an Expression System and Expression of a Model Gene As a model system, the open reading frame (ORF) of the mtr *N. crassa* gene was placed under the control of the al-3 promoter in plasmids designated pLRN and pALN and transformed into *N. crassa* under conditions which permit the mtr gene to provide, itself, a selectable marker function. Transformation of *N. crassa* with these vectors resulted in superior growth in the presence of light and in enhanced production of mRNA encoding the mtr gene product. The following describes the construction and expression.

*N. crassa* strain 82–59 (trp-2, mtr⁻, cot-1, ylo-a) obtained from D. D. Stadler, U. of Washington at Seattle was used as host. This strain requires tryptophan for growth and has a nonrevertable mtr⁻ phenotype containing a small deletion at site 1536 in the mtr ORF. Thus, this mutant cannot grow in the absence of tryptophan, and cannot grow even in the presence of tryptophan when excess arginine is present unless mtr functionality is restored.

The host strain was maintained on conidia growth slants in medium containing 1×Vogel's Medium, 2% sucrose, 0.05 mg/ml tryptophan.

Two plasmids were constructed placing the mtr ORF under control of the al-3 promoter. pLRN was constructed by ligating a 1.2 kb PstI/SalI fragment containing the al-3 promoter retrieved from 1.0 µg of an M13mp18 vector provided by Guiseppe Macino, University of Rome and gel purified using Gene Clean II Kit (Bio 1011), into a PstI/SalI digest of 1 µg plasmid pN846 described in detail in U.S. Ser. No. 08/105,448, now abandoned, filed Aug. 12, 1993 and PCT WO 93/25663 cited above. The complete sequence of the al-3 promoter-containing insert is shown in FIG. 1. Dr. Macino has identified the region responsible for photoinduction to reside between positions −55 to −225 from the transcription start site. The digested materials were incubated overnight at 15° C. with 400 U of T4 ligase. The ligation mixture was transformed into *E. coli* DH5A made competent with treatment by calcium chloride and transformed colonies were screened for the insert using restriction digest analysis.

The linearized vector obtained by PstI/SalI digest of pN846 provides a portion of the mtr promoter, the entire ORF and terminator sequences. Ligation of this fragment with the 1.2 kb al-3 promoter fragment places the mtr ORF under control of the al-3 promoter. The resulting vector was designated pLRN (for light regulated neutral).

An analogous vector was also prepared placing the al-3 promoter 5' of the complete mtr insert in pN846, thus effectively 5' of the native mtr promoter. In this plasmid, the complete mtr promoter is located between SalI sites at positions 1336–1660, i.e., between the al-3 promoter and the mtr ORF. This plasmid was designated pALN.

Spheroplasts of strain 82–59 were prepared using the methods described by Vollmer, S. J. et al. *Proc Natl Acad Sci USA* (1986) 83:4869–4873. Transformation was conducted as described by Stuart, W. D. et al. *Genome* (1988) 30:188–203.

Selection was conducted using bottom plates made with Vogel's Media and FIGS (0.5% fructose, 0.2% inositol, 0.5% glucose, 20% sorbose) as the carbon source, and in the presence of 0.1 mg/ml arginine and 0.01 mg/ml tryptophan. The cultures were incubated in a light-sealed 28° C. incubator. Regulation of light conditions was accomplished with a Micronta Programmable Timer (Radio Shack Catalog No. 63-864) to cycle the light every two hours. Colonies were scored after two days and transferred to high selection conidial growth media on slants. In the presence of sorbose, *N. crassa* takes on a colonial phenotype which permits isolation of a single transformed cell. Minimal top agar (1M sorbitol, 1× Vogel's salts and 2.8% bacto agar) was also supplemented with 0.1 mg/ml arginine.

The transformation frequencies per $4.6 \times 10^6$ cells were approximately 20 and 70 for pLRN and pALN respectively.

Homokaryotic transformants were obtained by transferring conidia to slants containing supplements of 0.05 mg/ml pfpa and 0.05 mg/ml anthranilic acid. (Anthranilic acid was added to obviate the trp-2 mutation; addition of tryptophan would have resulted in competition with pfpa for the transport system.) These were checked for sensitivity to pfpa in the presence of light. A conidia suspension of colonies that showed light sensitivity were plated on the high selection medium described above which includes 0.1 mg/ml arg and 0.01 mg/ml trp in order to isolate homokaryotic transformed cells. Plating and restreaking was repeated until 100% sensitivity to pfpa in the light was obtained and successful growth on high selection media was observed. This ensures isolation of homokaryons.

The resulting homokaryons were examined for the effect of light on conidial growth. Liquid Vogel's minimal medium (1× Vogel's salts and 2% sucrose) supplemented with 0.015 mg/ml pfpa and 0.05 mg/ml anthranilic acid was inoculated with either 30,000 or 60,000 conidia and cultured in the light and dark at 28° C. for 5 days. The fungi were then harvested by filtration and the dry weight of cell mass measured. Wild type strain 74a was used as a control.

Figure 3:
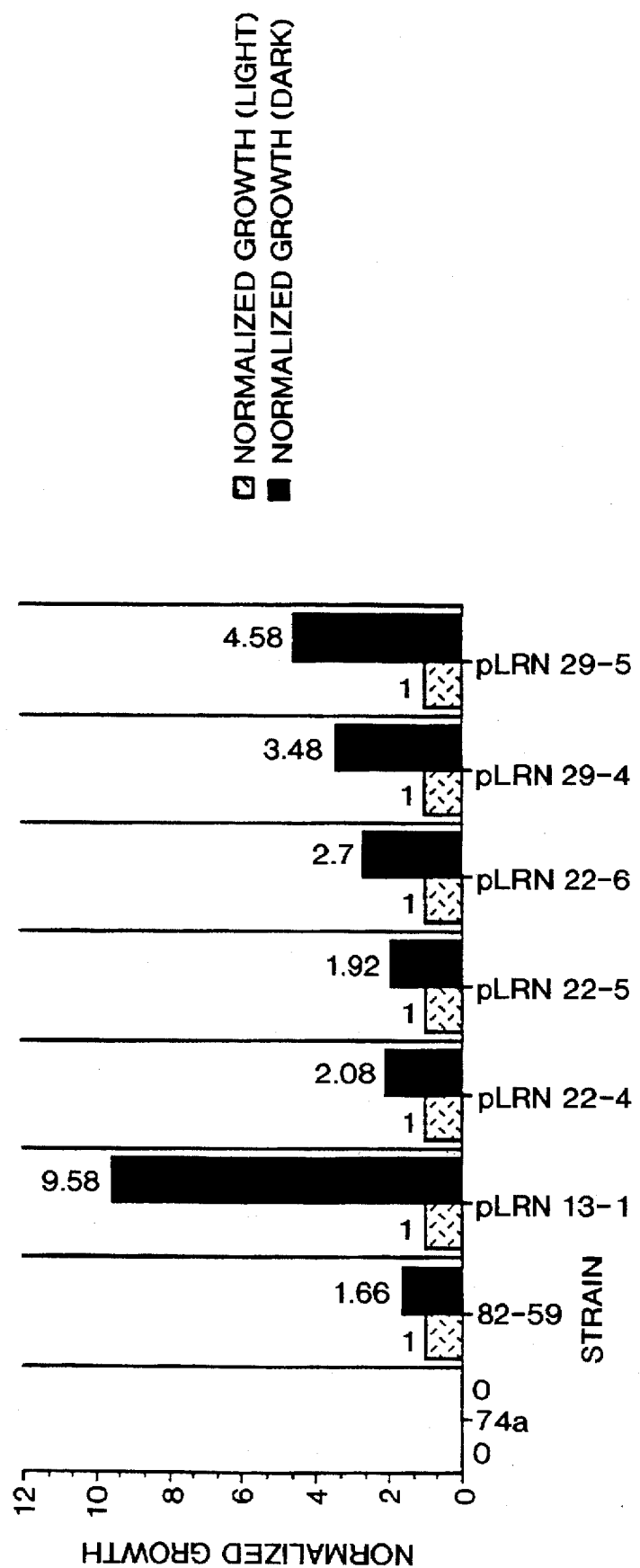
FIG. 3 is an alternative form of the data in FIG. 2 wherein the growth in darkness has been normalized.
Figure 4:
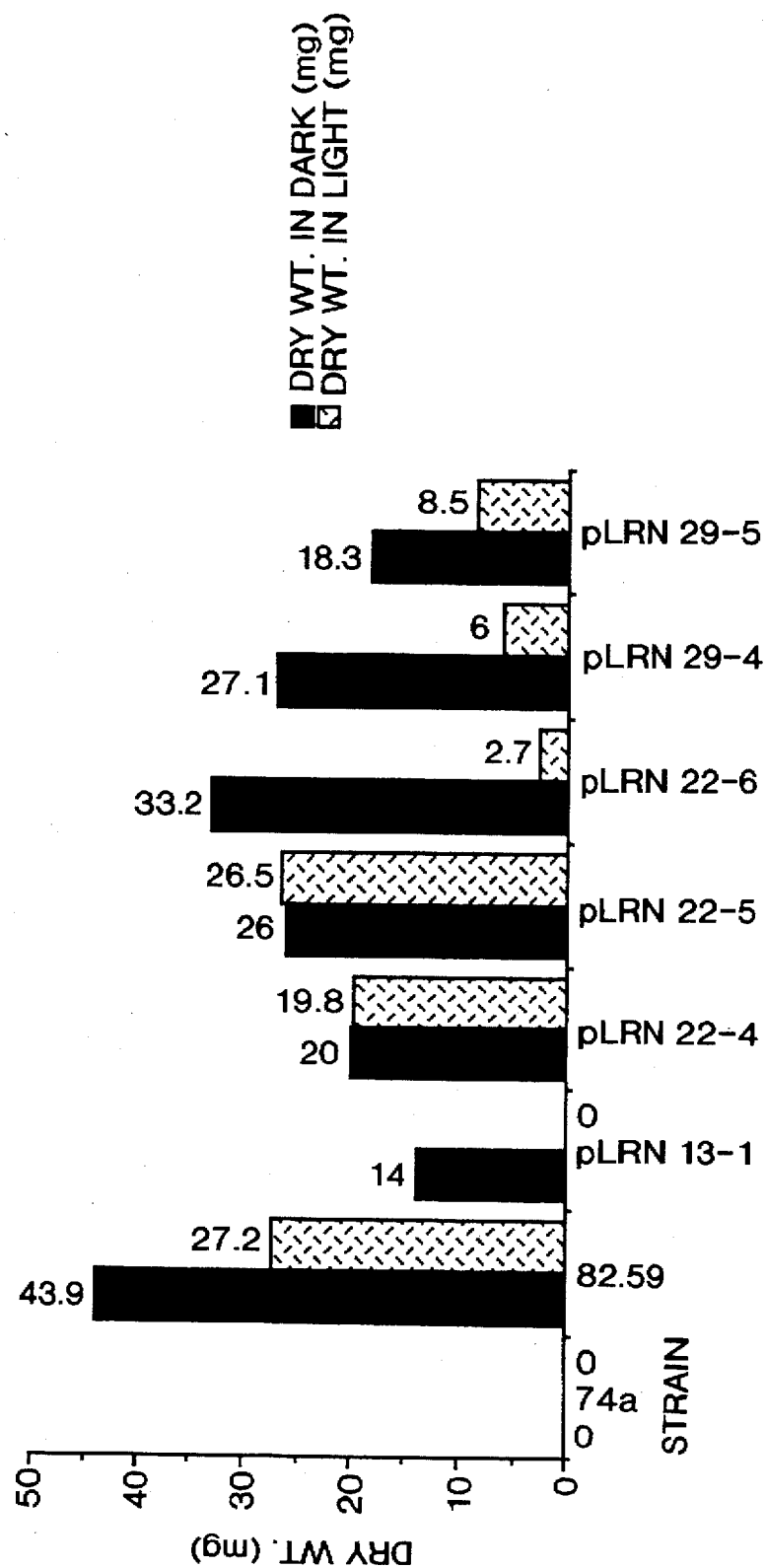
FIG. 4 shows the data obtained in an experiment similar to that depicted in FIG. 2 with a fresh culture of the untransformed strain.
Figure 5:
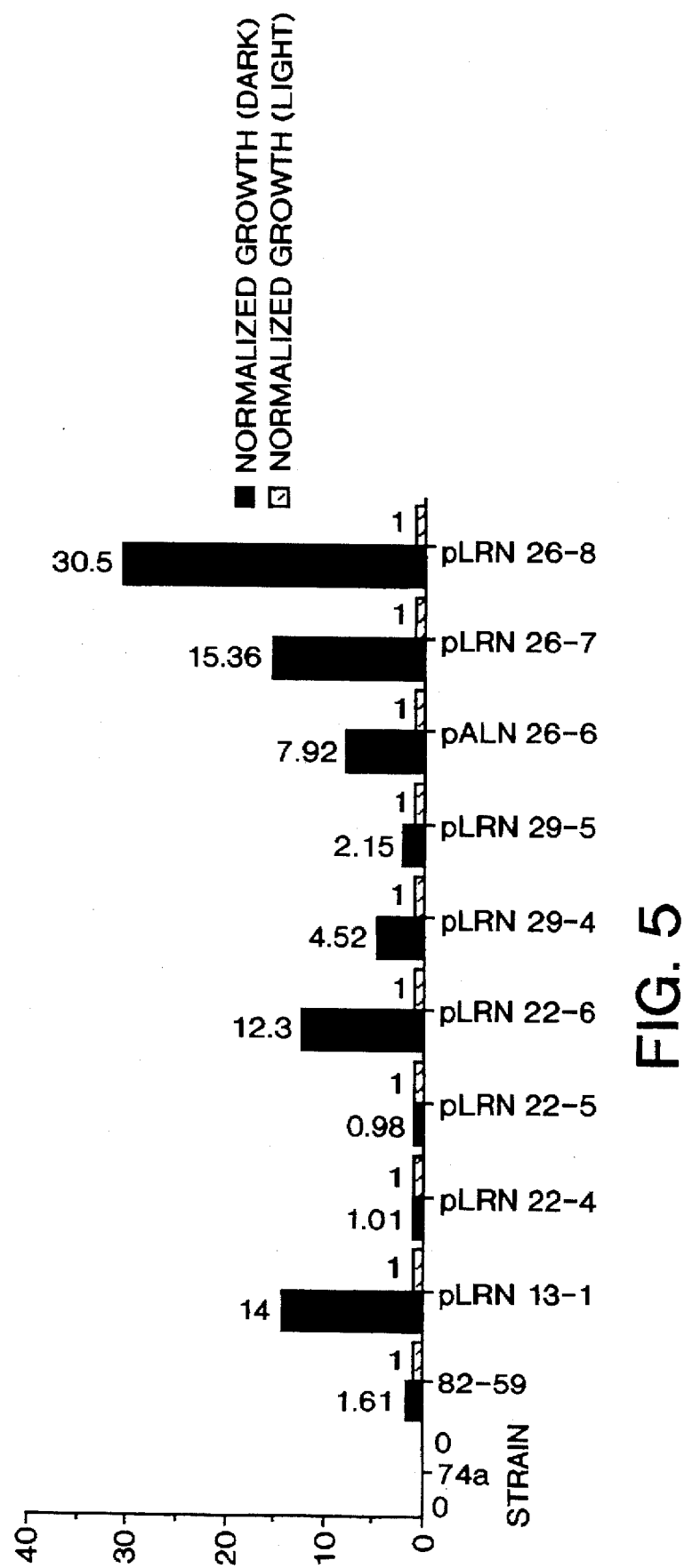
FIG. 5 is an alternative form of the data in FIG. 4 wherein the growth in darkness has been normalized.

The results are shown in FIG. 2. An alternate form of these results where growth in light is normalized to 1 mg is shown in FIG. 3. As expected, wild type strain 74a is always sensitive to pfpa and thus does not grow. The untransformed strain 82–59 is relatively tolerant to pfpa since it has a nonrevertable mtr⁻ phenotype. The selected homokaryons show a greater differential between light and dark growth since in the dark, their mtr⁻ phenotype is retained, while in the light the mtr gene is expressed rendering them susceptible to pfpa poisoning. Thus, as indicated, a number of the transformed strains showed a greater light sensitivity as compared to the parental strain 82–59. This experiment was repeated with a fresh culture of the untransformed strain 82–59 to obtain similar results as shown in FIG. 4; the normalized results obtained in FIG. 4 are shown in FIG. 5.

The transformed pLRN 13-1 was selected for further study since it showed the greatest differential between light and dark conditions.

Messenger RNA from pLRN13-1 and 82–59 was subjected to Northern Blot analysis and probed with 1050 bp of the mtr ORF. The results for pLRN13-1 showed a high level of production of mRNA hybridizing with the probe in the presence of light, but very little in the dark. Strain 82–59 did not show production of mtr mRNA under either condition.

Thus, using the mtr coding sequence as a model system, it is demonstrated that al-3 can regulate the expression of this ORF as a function of the presence of light.

Example 2
Expression of a Mammalian Gene

The mammalian gene encoding chymosin was placed in operable linkage with the al-3 promoter as shown in FIG. 6.

A 1 μg sample of the 6.6 kb plasmid pLRN was digested with SalI and purified. SalI cleaves between the al-3 promoter and the mtr ORF. The chymosin gene was released with XhoI and SalI from a cDNA chymosin clone obtained from Berlex Biosciences and gel purified. The DNA sequence encoding chymosin is shown in FIG. 7. The ORF extends from the ATG at position 72 to the TGA at position 1218. The chymosin ORF was ligated in proper orientation in the cleaved vector providing the intermediate pCLRN containing the chymosin ORF immediately downstream and in operable linkage to the al-3 promoter and immediately upstream of the mtr ORF. Proper insertion was verified by restriction analysis. pCLRN was digested with HincII and recircularized with 400 U of T4 ligase. This deletes approximately 1.1 kb of the mtr ORF. The resulting 6.6 kb plasmid was designated pLRC. pLRC thus contains an expression system for chymosin under control of the al-3 promoter contiguous with a nonfunctional portion of the mtr ORF sufficient to effect homologous recombination.

The host spheroplasts were obtained from strain His-3 TM428A, FGSC4438. This mutant will grow only in the presence of histidine and a plasmid capable of restoring histidine biosynthesis, pNH60, containing the his gene and obtained from FGSC, was used for cotransformation selection. Transformation was conducted using 10 μg pLRC DNA and 2 μg of pNH60 DNA as described above. The transformants were selected as described above using bottom plates and top agar made with Vogel's Media and FIGS in the absence of amino acid supplements. This resulted in isolation of 44 transformants. An inoculum of each into 1× Vogel's with 2% sucrose liquid medium was made and the cultures were incubated at 28° C. for 7 days in constant 2-hour light cycling.

For 41 of the transformants, 1 ml of liquid medium was blotted onto MSI charged nylon membrane using the Minifold-II Slot Blot System. The filter was treated with TBS (20 mM tris-HCl, 500 mM NaCl) and 10 mM EDTA, pH 8.0 and incubated at 70° C. for 30 minutes to inactivate endogenous alkaline phosphatase.

The filter was rinsed in TBS and blocked using 10% nonfat dry milk in TBS for 1 hour at 37° C. The block was drained and the primary antibody (rabbit anti-prochymosin) at a 1:5000 dilution in 5% nonfat milk TBS was added and the mixture incubated at 37° C. for 1 hour. The filter was drained and washed in 0.05% TWEEN TBS (TTBS) 2 times (5 minutes). The secondary antibody (goat antirabbit alkaline phosphatase conjugate) was added at a final concentration of 0.24 pg/ml and incubated at 37° C. for 1 hour. The filter was washed and the color substrate added according to the instructions of the manufacturer (Boehringer Mannheim Genius Kit) (45 μl of 75 mg/ml Nitroblue tetrazolium salt, 35 μl of 50 mg/ml 5-bromo-4-chloro-3-indolylphosphate diluted in 10 ml of 100 mM tris-HCl, 100 mM NaCl and 50 mM $MgCl_2$, pH 9.5).

The results showed that 27 of the 41 transformants produced chymosin. However, when 6 of these producers were selected and assayed by SDS PAGE (Western Blot), no chymosin was detected. The experiment was repeated using 3 of the selected strains and culturing 9 days at 28° C. in light cycled as above. 450 μl of liquid media were treated with various concentrations of 0.5–2M KCl to release proteins from cell walls and analyzed by the Slot Blot method described above. In addition, several cultures were treated with 50 μg/ml lysozyme to cause apical swelling and lysis of the mycelia. Slot Blot analysis of each of these cultures treated of showed higher detection of chymosin.

---

We claim:

1. A nucleic acid molecule for expression of a first nucleotide sequence encoding a heterologous protein in a filamentous fungus, which nucleic acid molecule comprises said first nucleotide sequence operably linked to the al-1, al-2 or al-3 promoter and optionally further comprises a second nucleotide sequence that provides for a selectable marker in said fungus.

2. The nucleic acid molecule of claim 1 wherein said second nucleotide sequence is present and promotes homologous recombination of said nucleic acid molecule with the fungus chromosome so as to alter a region of said chromosome thus providing a selectable marker.

3. The nucleic acid molecule of claim 2 wherein said second sequence is contiguous with said first sequence.

4. The nucleic acid molecule of claim 2 wherein said second sequence corresponds to at least a portion of the mtr locus.

5. The nucleic acid molecule of claim 1 wherein said second sequence is present and encodes a protein that confers a selectable characteristic on said fungus.

6. The nucleic acid molecule of claim 5 wherein said selectable characteristic is conferred by the product of the mtr gene.

7. The nucleic acid molecule of claim 1 wherein said first sequence encodes chymosin or relaxin.

8. A Neurospora fungus modified to contain the nucleic acid molecule of claim 1.

9. A method to produce proteins heterologous to a Neurospora fungus, which method comprises culturing the Neurospora fungus of claim 8 under conditions wherein said heterologous protein is produced; and recovering the heterologous protein from the culture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1237 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AAGCTTGCAT  GCCTGCAGCT  TTATGCACTC  GGCGCTTTCC  TGTGTCAAGT  CTTGCATCGC    60

CGACAGACGT  GCACAAAGTC  GCCGCGTGTG  TGCTTGAATC  CGTTGCCATC  GAGTGCTATA   120

TAAAGTGTCC  AGACGTCCCC  TTTCCTAAAT  CGTCTTGAAT  GTCCCAATAT  GCATGGATGA   180

AGTGGACTGA  ACTCGCACGT  TCGACCGCTT  TTCTGGAATA  CCCCTAATTT  GCGCAAGGTC   240

CCACAACAGC  CGACCTCGTT  CAACATCTCT  TACCACCTAC  AGTTACCTAC  CCATTTTGA   300

CGAGCCCCTT  ACCAGCAACA  ACGCGTCAAT  CCTTGGTTAT  TCTCTGTTTG  TTCATGTCGG   360

TCTGAAGCCC  TGACAAGACA  ACATCACAGC  AGAAATTTGA  ACGCTTTTCC  ACAAACTACA   420

AGGTGAGAAA  CCCTCCCCAG  TTTTCATCCC  TAGAAGATGC  CGGTTTCAGC  AGGGAGCTCC   480

CGACAAAGAG  CGCGCGAGAC  GGGATCGCCC  GTTCGATCTT  CAGTTGTGAA  GCTCTTTTGT   540
```

-continued

| | | | | | |
|---|---|---|---|---|---|
| CCCCCTGTGA | GAGCTCCCGC | CCCGCATCTG | AAACCCCACC | ACGCTACTTT | CAGGTGTCGT | 600
| CGGGGTTTCA | TTCTTGCAAA | CATGTCCTCC | GTCGGCCGCC | CAAGAAGTCT | CCGCACTTGC | 660
| AATCACCTTG | CATCCACTGC | CAGGGGAAAG | GAAAGGACAG | GCAGGTCAGA | TCTGAGGAAA | 720
| GCGCTACGGC | AGCTTGATCC | GATTGTCCG | CCCCTAGTTT | CCCTTCTGAT | CGCTTCGAGG | 780
| ATCCAGTGAC | GATGGCTGGC | ATGTGACAAG | ATCGGGGGAT | GCAATCTCGA | GTTTTCTGGA | 840
| ACCTAGCAGA | AAGAGGCCTT | CTTTCCATTC | GGCGTATTCT | TTGCTGACCC | CAGATACAGA | 900
| TAGATCTCTT | GGCCTTTGTT | CACTCAGCAG | GCAAGCAGGG | CAAATCCCCC | TTCTCATAGC | 960
| AAAGTGAGGT | CGATTGCTGT | CGATTGGCAC | ACGACCTGTC | AAGCGGTATT | ATCGTCATAG | 1020
| CGTGCGGGTA | TCGAATATTG | CCCCCGAGAC | CGTGAAGCTT | GCCTCCGGTT | GTCACACAGC | 1080
| ACGTCAAGTA | ATTATAAGAA | GCCAGCCAGA | GCGCCGGCCA | CTTTGGATCA | GACGACGCAC | 1140
| GGGGTTAGCA | TCCTCTACAG | TACCGACGGG | TTTCCAATAA | GTCGACTCTA | GACTTAATTA | 1200
| AGGATCCGGC | GCGCCCCGG | GTACCGAGCT | CGAATTC | | | 1237

( 2 ) INFORMATION FOR SEQ ID NO:2:

( i ) SEQUENCE CHARACTERISTICS:
        ( A ) LENGTH: 1240 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| | | | | | |
|---|---|---|---|---|---|
| GAATTCGAGC | TCGGTACCCG | GGGATCCTCT | AGCCTCGAGG | CTAGAGTCTC | CCGGCTGGAC | 60
| CCAGATCCAA | GATGAGGTGT | CTCGTGGTGC | TACTTGCTGT | CTTCGCTCTC | TCCCAGGGCG | 120
| CTGAGATCAC | CAGGATCCCT | CTGTACAAAG | GCAAGTCTCT | GAGGAAGGCG | CTGAAGGAGC | 180
| ATGGGCTTCT | GGAGGACTTC | CTGCAGAAAC | AGCAGTATGG | CATCAGCAGC | AAGTACTCCG | 240
| GCTTCGGGGA | GGTGGCCAGC | GTGCCCCTGA | CCAACTACCT | GGATAGTCAG | TACTTTGGGA | 300
| AGATCTACCT | CGGGACCCCG | CCCCAGGAGT | TCACCGTGCT | GTTTGACACT | GGCTCCTCTG | 360
| ACTTCTGGGT | ACCCTCTATC | TACTGCAAGA | GCAATGCCTG | CAAAAACCAC | CAGCGCTTCG | 420
| ACCCGAGAAA | GTCGTCCACC | TTCCAGAACC | TGGGCAAGCC | CCTGTCTATC | CACTACGGGA | 480
| CAGGCAGCAT | GCAGGGCATC | CTAGGCTATG | ACACCGTCAC | TGTCTCCAAC | ATTGTGGACA | 540
| TCCAGGAGAC | AGTAGGCCTG | AGCACCCAGG | AGCCGGGGA | CGTCTTCACC | TATGCCGAAT | 600
| TCGACGGGAT | CCTGGGGATG | GCCTACCCCT | CGCTCGCCTC | AGAGTACTCG | ATACCCGTGT | 660
| TTGACAACAT | GATGAACAGG | CACCTGGTGG | CCCAAGACCT | GTTCTCGGTT | TACATGGACA | 720
| GGAATGGCCA | GGAGAGCATG | CTCACGCTGG | GGGCCATCGA | CCCGTCCTAC | TACACAGGGT | 780
| CCCTGCACTG | GGTGCCCGTG | ACAGTGCAGC | AGTACTGGCA | GTTCACTGTG | GACAGTGTCA | 840
| CCATCAGCGG | TGTGGTTGTG | GCCTGTGAGG | GTGGCTGTCA | GGCCATCCTG | GACACGGGCA | 900
| CCTCCAAGCT | GGTCGGGCCC | AGCAGCGACA | TCCTCAACAT | CCAGCAGGCC | ATTGGAGCCA | 960
| CACAGAACCA | GTACGATGAG | TTTGACATCG | ACTGCGACAA | CCTGAGCTAC | ATGCCCACTG | 1020
| TGGTCTTTGA | GATCAATGGC | AAAATGTACC | CACTGACCCC | CTCCGCCTAT | ACCAGCCAAG | 1080
| ACCAGGGCTT | CTGTACCAGT | GGCTTCCAGA | GTGAAAATCA | TTCCCAGAAA | TGGATCCTGG | 1140
| GGGATGTTTT | CATCCGAGAG | TATTACAGCG | TCTTTGACAG | GGCCAACAAC | CTCGTGGGGC | 1200
| TGGCCAAAGC | CATCTGACTC | GTCGACCTGC | AGCCAAGCTT | | | 1240